United States Patent
Kiers et al.

(10) Patent No.: US 7,738,103 B2
(45) Date of Patent: Jun. 15, 2010

(54) INSPECTION METHOD AND APPARATUS, LITHOGRAPHIC APPARATUS, LITHOGRAPHIC PROCESSING CELL AND DEVICE MANUFACTURING METHOD FOR DETERMINING A PARAMETER OF A TARGET PATTERN

(75) Inventors: Antione Gaston Marie Kiers, Veldhoven (NL); Arie Jeffrey Den Boef, Waalre (NL); Hugo Augustinus Joseph Cramer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 12/258,719

(22) Filed: Oct. 27, 2008

(65) Prior Publication Data
US 2009/0135424 A1    May 28, 2009

Related U.S. Application Data

(60) Provisional application No. 60/996,278, filed on Nov. 8, 2007.

(51) Int. Cl.
*G01B 9/08* (2006.01)
*G01B 11/00* (2006.01)
*G01N 21/00* (2006.01)

(52) U.S. Cl. .................. 356/392; 356/394; 356/237.3; 356/601

(58) Field of Classification Search ......... 356/388–394, 356/237.1–237.5, 600–630, 445–448, 243.1, 356/243.8; 355/53, 55; 702/27, 159, 127, 702/172
See application file for complete search history.

(56) References Cited

U.S. PATENT DOCUMENTS

| | | | |
|---|---|---|---|
| 6,721,691 B2 | 4/2004 | Bao et al. | |
| 6,795,193 B2 * | 9/2004 | Schulz | 356/445 |
| 6,842,261 B2 * | 1/2005 | Bao et al. | 356/636 |
| 7,148,959 B2 * | 12/2006 | Dusa et al. | 356/237.4 |
| 7,187,796 B1 * | 3/2007 | Phan et al. | 382/144 |
| 7,221,989 B2 * | 5/2007 | Prager et al. | 700/108 |
| 7,460,237 B1 * | 12/2008 | Cramer | 356/445 |
| 2007/0298335 A1 * | 12/2007 | Sawai et al. | 430/30 |

FOREIGN PATENT DOCUMENTS

EP    1 628 164 A2    2/2006

\* cited by examiner

*Primary Examiner*—Sang Nguyen
(74) *Attorney, Agent, or Firm*—Sterne, Kessler, Goldstein & Fox P.L.L.C.

(57) ABSTRACT

In a method for determining a structure parameter of a target pattern, a first series of calibration spectra are determined from at least one reference pattern, each spectra being determined using a different known value of at least one structure parameter of the respective reference pattern. The first series of calibration spectra does not take into account parameters of an apparatus used to produce the reference pattern. A representation of each of the first series calibration spectra is stored in a central library. A second series of calibration spectra corresponding to at least one of the stored spectra for a target spectrum is determined using the parameters of the apparatus for measuring the target spectrum. A measured target spectrum is produced by directing a beam of radiation onto the target pattern. The measured target spectrum and the second series of calibration spectra are compared, where this comparison is used to derive a value for the structure parameter of the target pattern.

12 Claims, 4 Drawing Sheets

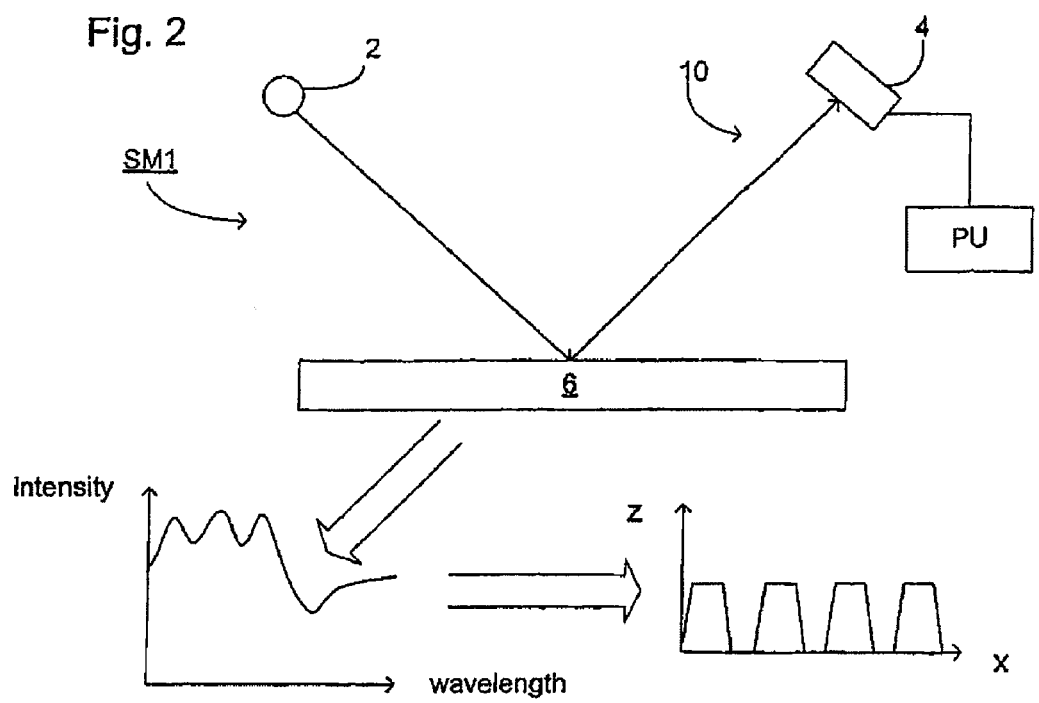
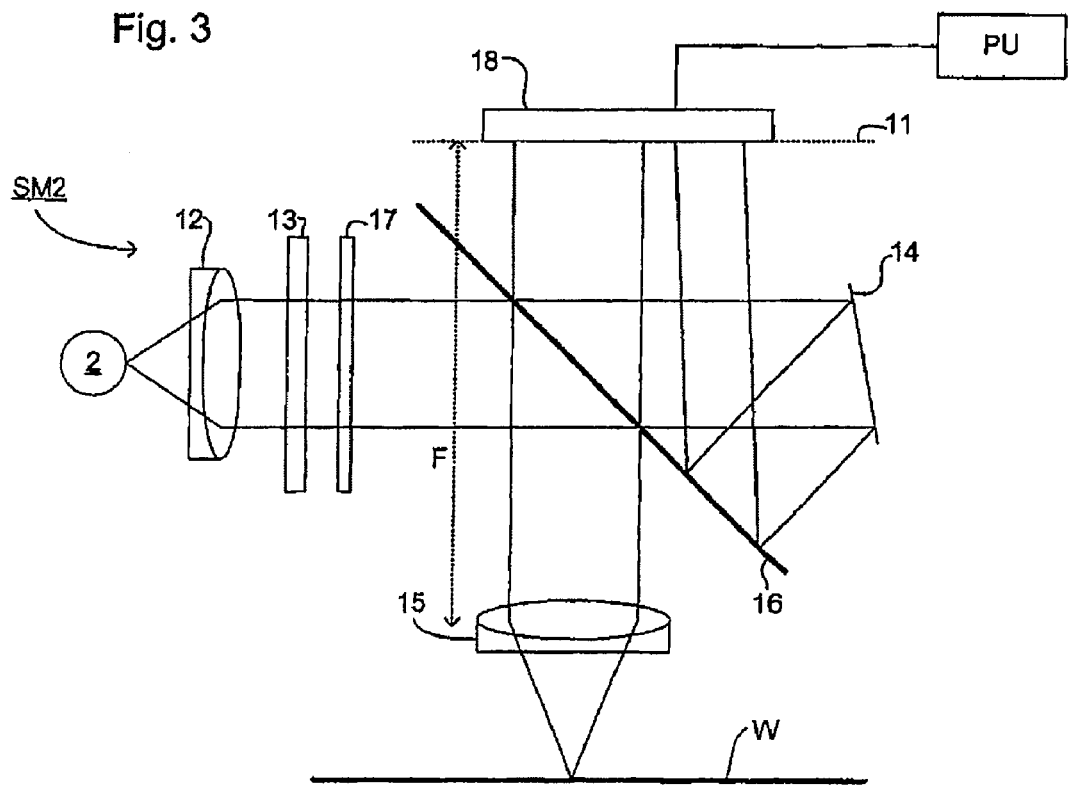

$$\begin{bmatrix} C_x \\ C_y \end{bmatrix} = \overbrace{\begin{bmatrix} z_1 & z_2 \\ z_3 & z_4 \end{bmatrix} \cdot \begin{bmatrix} y_1 & y_2 \\ y_3 & y_4 \end{bmatrix}}^{\text{Tool dependent}} \cdots \overbrace{\begin{bmatrix} S_1 & S_2 \\ S_3 & S_4 \end{bmatrix}}^{\text{Tool Independent}} \cdots \overbrace{\begin{bmatrix} b_1 & b_2 \\ b_3 & b_4 \end{bmatrix} \cdot \begin{bmatrix} a_1 & a_2 \\ a_3 & a_4 \end{bmatrix}}^{\text{Tool dependent}} \cdot \begin{bmatrix} I_x \\ I_y \end{bmatrix}$$

$$\begin{bmatrix} C_x \\ C_y \end{bmatrix} = \begin{bmatrix} after_1 & after_2 \\ after_3 & after_4 \end{bmatrix} \cdot \begin{bmatrix} S_1 & S_2 \\ S_3 & S_4 \end{bmatrix} \cdot \begin{bmatrix} before_1 & before_2 \\ before_3 & before_4 \end{bmatrix} \cdot \begin{bmatrix} I_x \\ I_y \end{bmatrix}$$

Fig. 5

INSPECTION METHOD AND APPARATUS, LITHOGRAPHIC APPARATUS, LITHOGRAPHIC PROCESSING CELL AND DEVICE MANUFACTURING METHOD FOR DETERMINING A PARAMETER OF A TARGET PATTERN

CROSS REFERENCE TO RELATED APPLICATION

This application claims benefit under 35 U.S.C. §119(e) to U.S. Provisional Patent Application No. 60/996,278, filed Nov. 8, 2007, which is incorporated by reference herein in its entirety.

FIELD

Embodiments of the present invention relate to methods of inspection that can be used, for example, in the manufacture of devices by lithographic techniques and to methods for manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a "mask" or a "reticle," may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (e.g., resist) provided on the substrate. In general, a single substrate will contain a network of adjacent target portions that are successively patterned. Known lithographic apparatus include so-called "steppers," in which each target portion is irradiated by exposing an entire pattern onto the target portion at one time, and so-called "scanners," in which each target portion is irradiated by scanning the pattern through a radiation beam in a given direction (e.g., the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate such as, for example, an overlay error between successive layers formed in or on the substrate. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This may be done, for example, by comparing the reflected beam with data stored in a library of known measurements associated with known substrate properties. Two main types of scatterometers are known. Spectroscopic scatterometers direct a broadband radiation beam onto the substrate and measure the spectrum (e.g., intensity as a function of wavelength) of the radiation scattered into a particular narrow angular range. Angularly-resolved scatterometers use a monochromatic radiation beam and measure the intensity of the scattered radiation as a function of angle. Polarized radiation beams may be used to generate more than one spectrum from the same substrate. Each library entry contains data representative of a pupil image which is, in turn, dependent on several metrology tool specific hardware parameters. These parameters include an angle of beam incidence, numerical aperture, wavelength range, polarization, illumination conformity, and noise. These parameters may vary between items of metrology hardware, even for the same type of scatterometer. Furthermore, these parameters may (for a single piece of metrology hardware) display a time variation due to wear-induced drifting of the metrology hardware parameters.

Thus, it is desirable for the library to contain parameters specific to the metrologies at all times. It is also desirable that the library include parameters relating to a profile of a grating that under measurement; that is, the library should contain information on the parameters relating to the sample with associated material parameters. If the calculation time of a library is, for example, about 30 minutes, then for 10 scatterometers of different parameters, 5 hours of calculation time is required.

U.S. Pat. No. 6,721,691 (the '691 patent), which is incorporated by reference herein in its entirety, discloses a method and system for incorporating the effects of small metrology hardware and material-based parameter variations in a library of simulated diffraction spectra. In particular, the '691 patent discloses a method for modifying the library diffraction spectra so as to be optimized for the particularly parameters of a specific piece of metrology hardware and specific samples. A parameter modification vector, which describes the differences between actual measurement parameters and parameters used in the calculation of the library spectra, is determined and used to calculate a corresponding modification to each library diffraction spectrum.

SUMMARY

It is desirable to provide a method for determining at least one process parameter of a lithographic process in which measured spectra are compared with determined spectra stored in a library, in which the calculation of the data stored in the library can be performed more efficiently.

According to an embodiment of the invention, there is provided a method for determining at least one parameter of a target pattern, where the method includes the following: calculating a first series of calibration spectra from at least one reference pattern, each of the spectra being determined using a different known value of at least one structure parameter of the respective reference pattern not taking account of the parameters of an apparatus used to produce the reference pattern; storing a representation of each of the spectra in a first library; calculating a second series of calibration spectra corresponding to at least one of the stored spectra for a target spectrum using the parameters of the apparatus for measuring the target spectrum; measuring a target spectrum produced by directing a beam of radiation onto the target pattern; comparing the measured target spectrum and the second series of calibration spectra; and, using the comparison to derive a value for the one parameter of the target pattern.

According to another embodiment of the invention, there is provided a method for producing a library for use in determining at least one parameter of a target pattern, where the method includes the following: calculating a first series of calibration spectra from at least one reference pattern, each of the spectra being determined using a different known value of at least one structure parameter of the respective reference pattern not taking account of the apparatus parameters used to produce the reference pattern; storing a representation of each of the spectra in a first library; calculating a second series of calibration spectra corresponding to at least one of the stored spectra for a target spectrum using the parameters of the apparatus used to measure the target spectrum; and, storing the second series of calibration spectra in a second library.

According to an embodiment of the invention, there is provided an inspection apparatus configured for determining the value of a parameter of a lithographic process used to manufacture a device layer on a substrate, where the apparatus includes the following: a first calculator configured to calculate a first series of calibration spectra from at least one reference pattern, each of the spectra being determined using a different known value of at least one structure parameter of the respective reference pattern not taking account of the apparatus parameters used to produce the reference pattern; a memory arrangement arranged to store a representation of each of the spectra in a first library; a second calculator configured to calculate a second series of calibration spectra corresponding to at least one of the stored spectra for a target spectrum using the parameters of the apparatus used to measure the target spectrum; a measurement module configured to target spectrum produced by directing a beam of radiation onto the target pattern; a comparison module configured to compare the measured target spectrum and the second series of calibration spectra; and, a derivation module configured to use the comparison to derive a value for the one parameter of the target pattern.

According to another embodiment of the invention, there is provided a computer program for implementing a method for determining at least one parameter of a target pattern, where the method includes the following: calculating a first series of calibration spectra from at least one reference pattern, each of the spectra being determined using a different known value of at least one structure parameter of the respective reference pattern not including parameters of an apparatus used to produce the reference pattern; causing a representation of each of the spectra to be stored in a first library; calculating a second series of calibration spectra corresponding to at least one of the stored spectra for a target spectrum using the parameters of the apparatus used to measure the target spectrum; combining the first series of calibration spectra and the second set of calibration spectra to produce a third set of calibration spectra which is representative of the spectra produced by the target spectra using the apparatus; comparing a measured target spectrum and the second series of calibration spectra; and, using the comparison to derive a value for the one parameter of the target pattern.

Further features and advantages of embodiments of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles of embodiments of the invention and to enable a person skilled in the relevant art(s) to make and use embodiments of the invention.

FIG. 2 depicts a scatterometer in which embodiments of the present invention may be implemented.

FIG. 3 depicts a scatterometer which embodiments of the present invention may be implemented.

FIG. 5 is an illustration of Jones matrices used to produce records for the library in accordance with an embodiment of the invention.

Figure 1A:
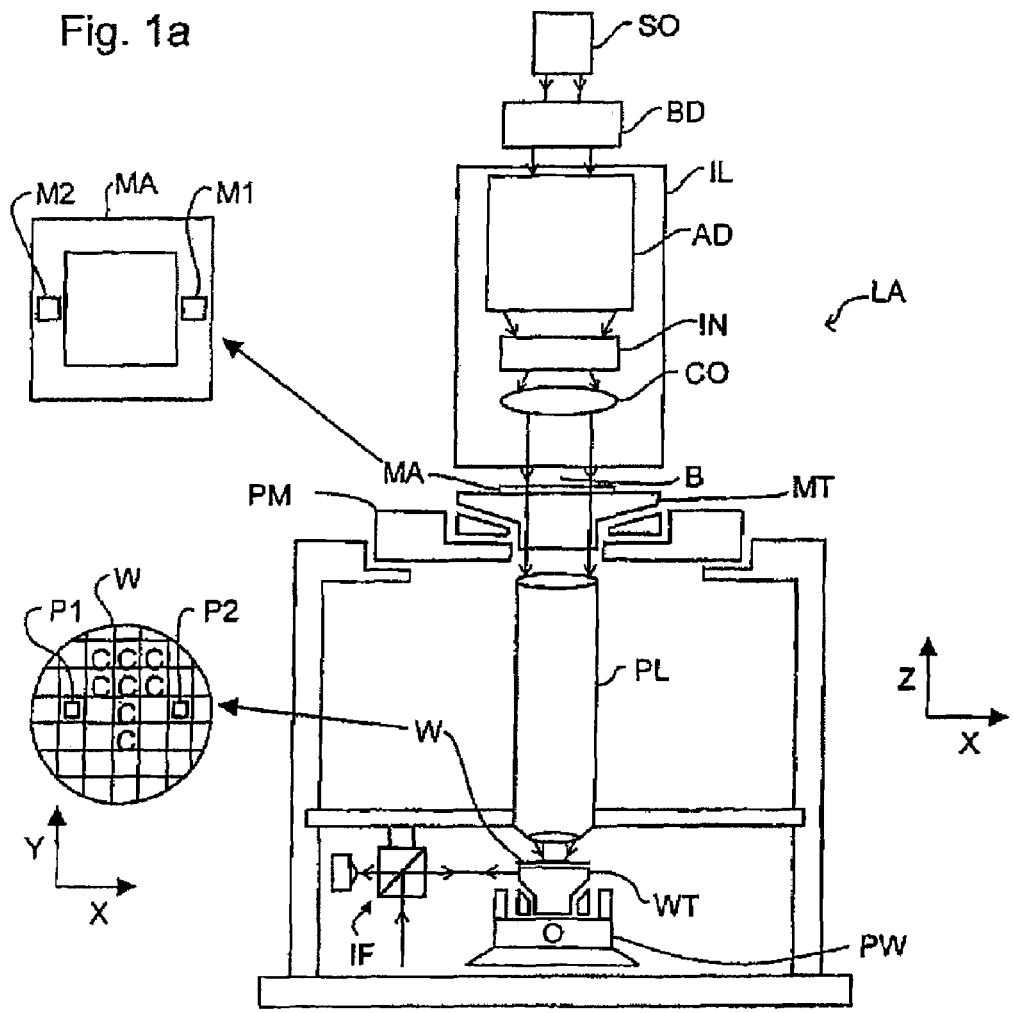
FIG. 1a depicts a lithographic apparatus in which embodiments of the present invention may be implemented.

The features and advantages of embodiments of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical, or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1a schematically depicts a lithographic apparatus which embodiments of the present invention may be implemented. The apparatus includes an illumination system (illuminator) IL configured to condition a radiation beam B (e.g., UV radiation or DUV radiation), a support structure or patterning device support (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure or patterning device support holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic, or other clamping techniques to hold the patterning device. The support structure may be a frame or a table, which, for example, may be fixed or movable as required. The support structure may ensure that the patterning device is at a desired position (e.g., with respect to the projection system). Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate (e.g., if the pattern includes phase-shifting features or so called assist features). Generally, the pattern imparted to the radiation beam will correspond to a particular functional layer in a device being created in the target portion such as, for example, an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type referred to above or employing a reflective mask).

The lithographic apparatus may be of a type having two (dual stage) or more substrate tables (and/or two or more mask tables). In such "multiple stage" machines, the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index (e.g., water) so as to fill a space between the projection system and the substrate. An immersion liquid may also be applied to other spaces in the lithographic apparatus (e.g., between the mask and the projection system). Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases, the source may be an integral part of the lithographic apparatus such as, for example, when the source is a mercury lamp. The source SO and the illuminator IL, together with the beam delivery system BD (if required) may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device (e.g., mask) MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately (e.g., so as to position different target portions C in the path of the radiation beam B). Similarly, the first positioner PM and another position sensor (which is not explicitly depicted in FIG. 1) can be used to accurately position the patterning device (e.g., mask) MA with respect to the path of the radiation beam B (e.g., after mechanical retrieval from a mask library, or during a scan). In general, movement of the support structure or patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure or patterning device support (e.g., mask table) MT may be connected to a short-stroke actuator only or may be fixed. Patterning device (e.g., mask) MA and substrate W may be aligned using mask alignment marks M1 and M2 and substrate alignment marks P1 and P2. Although the substrate alignment marks as illustrated occupy dedicated target portions, they may be located in spaces between target portions (also known as scribe-lane alignment marks). Similarly, in situations in which more than one die is provided on the patterning device (e.g., mask) MA, the mask alignment marks may be located between the dies.

The depicted apparatus could be used in at least one of the following modes:

1. In step mode, the support structure or patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the x- and/or y-direction so that a different target portion C can be exposed. In step mode, the maximum size of the exposure field limits the size of the target portion C imaged in a single static exposure.

2. In scan mode, the support structure or patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the support structure or patterning device support (e.g., mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure or patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device such as, for example, a programmable mirror array of a type referred to above.

Combinations and/or variations on the above described modes of use or entirely different modes of use may also be employed.

Figure 1B:
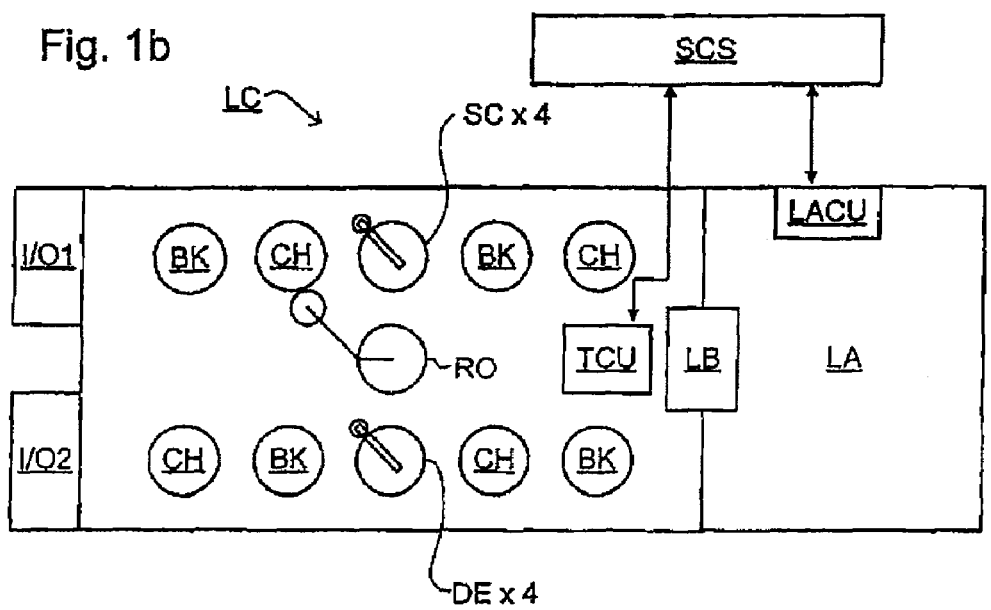
FIG. 1b depicts a lithographic cell or cluster in which embodiments of the present invention may be implemented.

FIG. 1b schematically depicts a lithographic cell in which embodiments of the present invention may be implemented. As shown in FIG. 1b, the lithographic apparatus LA forms part of the lithographic cell LC, also sometimes referred to a lithocell or cluster, which also includes apparatus to perform pre- and post-exposure processes on a substrate. Conventionally, these include spin coaters SC to deposit resist layers, developers DE to develop exposed resist, chill plates CH and bake plates BK. A substrate handler, or robot, RO picks up substrates from input/output ports I/O1 and I/O2, moves them between the different process apparatus and delivers them to the loading bay LB of the lithographic apparatus. These devices, which are often collectively referred to as the track, are under the control of a track control unit TCU, which is controlled by a supervisory control system SCS. The SCS also controls the lithographic apparatus via a lithography control unit LACU. Thus, the different apparatus can be operated to maximize throughput and processing efficiency.

In order to ensure that the substrates exposed by the lithographic apparatus are exposed correctly and consistently, it is desirable to inspect exposed substrates to measure properties such as, for example, overlay errors between subsequent layers, line thicknesses, and critical dimensions (CD). If errors are detected, adjustments may be made to exposures of subsequent substrates, especially if the inspection can be prior to other substrates in the same batch are exposed. Also, already exposed substrates may be stripped and reworked (e.g., to improve yield or discard), thereby avoiding performing exposures on faulty substrates. In a case where only some target portions of a substrate are faulty, further exposures can be performed only on those target portions which are considered good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable rapid measurements, it is desirable that the inspection apparatus measure properties in the exposed resist layer immediately after the exposure. However, a latent image in the resist has a very low contrast (i.e., there is only a very small difference in refractive index between the parts of the resist which have been exposed to radiation and those which have not) and not all inspection apparatus have sufficient sensitivity to make adequate measurements of the latent image. Therefore, measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image (at which point either the exposed or unexposed parts of the resist have been removed) or after a pattern transfer step such as etching. The latter possibility limits the possibilities for rework of faulty substrates but may still provide useful information.

FIG. 2 depicts a scatterometer SM1 which may be used in an embodiment of the present invention. It includes a broadband (white light) radiation projector 2 which projects radiation onto a substrate 6. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU (e.g., by Rigorous Coupled Wave Analysis and non-linear regression or by comparison with a library of simulated spectra as shown at the bottom of FIG. 2). In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer SM2 that may be used in accordance with an embodiment of the present invention is shown in FIG. 3. In this device, the radiation emitted by radiation source 2 is focused using lens system 12 through interference filter 13 and polarizer 17, reflected partially by reflected surface 16 and focused onto substrate W via a microscope objective lens 15, which has a high numerical aperture (NA) (e.g., at least 0.9 or at least 0.95). Immersion scatterometers may have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15; however, the pupil plane may be re-imaged with auxiliary optics (not shown) onto the detector. The pupil plane is the plane in which the radial position of radiation defines the angle of incidence and the angular position defines an azimuth angle of the radiation. The detector may be a two-dimensional detector so that a two-dimensional angular scatter spectrum of a substrate target can be measured. The detector 18 may be, for example, an array of CCD or CMOS sensors, and may use an integration time of, for example, 40 milliseconds per frame.

A reference beam is often used, for example, to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), separately at multiple wavelengths, or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths) is possible, which gives a large etendue, allowing a mixing of multiple wavelengths. The plurality of wavelengths in the broadband may each have a bandwidth of $\delta\lambda$ and a spacing of at least $2\delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations may manifest themselves into a variation in the printed grating. Accordingly, the scatterometry data of the printed gratings is used to reconstruct the gratings. The parameters of the grating, such as line widths and shapes, may be input to the reconstruction process, which is performed by processing unit PU from knowledge of the printing step and/or other scatterometry processes.

Figure 4:
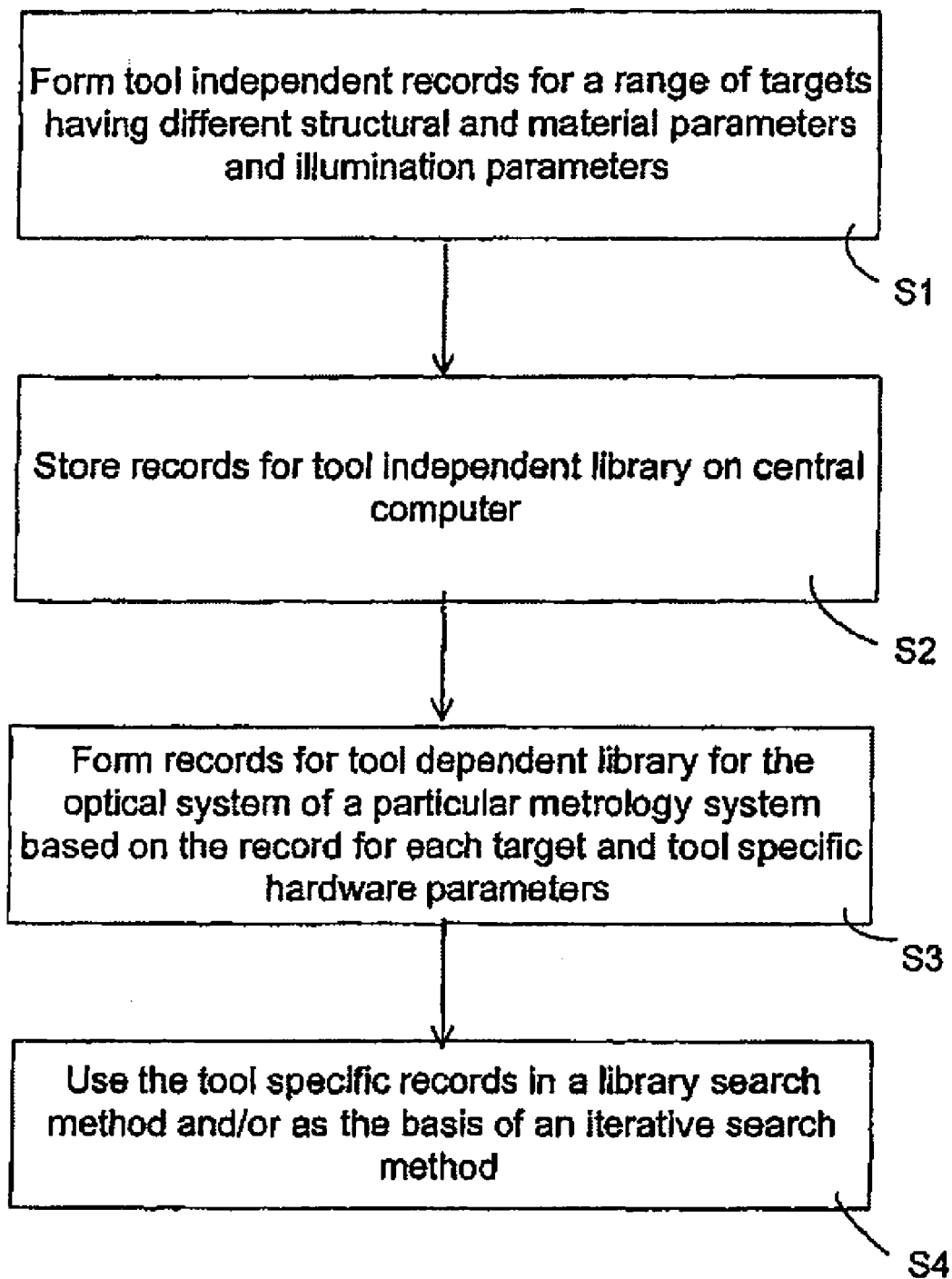
FIG. 4 depicts a method of setting up a library in accordance with an embodiment of the invention.

Referring to FIG. 4, an embodiment of a method is illustrated that may provide a computational savings by providing a tool independent library for each specific target (e.g., a grating on a specific set of underlying layers, which then may be used to form a tool dependent library that accounts for metrology hardware parameters). As the tool independent library may be applied to, for example, hundreds or even thousands of wafers with a particular target on a particular set of layers, even though the tool dependent library may need to be redetermined for each wafer (or batch of wafers), the method of FIG. 4 may lead to a significant computational saving. The tool independent library formed or created in procedure S1 of FIG. 4 may include records for a modeled pupil image for each possible combination of values of parameters for the target (e.g., critical dimension (CD), resist height and side wall angle (SWA), each of which parameters may vary across a range, together with parameters relating to the underlying layers). Each record may contain a set of spectra (e.g., in the form of pixel maps) with separate spectra for light reflected from the target for each diffraction order (e.g., −2, −1, 0, +1 and +2) and each polarization state (i.e., p and s components). Thus, the tool independent library may contain a very large number of entries which is stored in a central computer for future use in procedure S2 of FIG. 4.

The records for the tool dependent library may be produced so as to be indicative of the metrology hardware to determine the values of the parameters of a measured spectrum. As indicated in procedure S3 of FIG. 4, the tool dependent library may include records corresponding to each record in the tool independent library corresponding, in turn, to each combination of values of parameters for the target together with tool specific hardware parameters. The spectra for each record in the tool dependent library may be a linear combination of the set of spectra for the record stored in the tool independent library as follows:

$$S_{tdl} = a_1 S_{til-2,p} + a_2 S_{til-2,s} + a_3 S_{til-1,p} \qquad (1)$$

where $a_1, a_2 \ldots$ are coefficients and $S_{til-2,p}, S_{til-2,s} \ldots$ are the spectra stored in the tool independent library for the various combinations of diffraction orders and polarizations.

The coefficients $a_1, a_2 \ldots$ in equation (1), which may be single values, pixel maps, or functions, may be obtained from calibration measurements and thus take into account particular metrology tool specific hardware parameters such as, for example, numerical aperture, illumination uniformity and polarization dependent objective transmission, at the time at which it is desired to measure the parameter of the target and derive the parameter value.

Each optical element in an optical arrangement such as, for example, the scatterometer shown in FIG. 3, may be represented by a Jones Matrix. When light crosses an optical element, the resulting polarization of emerging light is found by taking the product of the Jones Matrix of the optical element and the Jones Vector of the incident light. Thus, considering the optical arrangement shown in FIG. 3, the relationship between the simulated signal [C] which will form the basis of the records in the library and the input signal [I] produced by the various optical elements shown in FIG. 3 may be represented by a set of multiplied Jones Matrices as follows:

$$\begin{bmatrix} C_x \\ C_y \end{bmatrix} = \begin{bmatrix} z_1 & z_2 \\ z_3 & z_4 \end{bmatrix} \cdot \begin{bmatrix} y_1 & y_2 \\ y_3 & y_4 \end{bmatrix} \cdots \begin{bmatrix} S_1 & S_2 \\ S_3 & S_4 \end{bmatrix} \cdots \begin{bmatrix} b_1 & b_2 \\ b_3 & b_4 \end{bmatrix} \begin{bmatrix} a_1 & a_2 \\ a_3 & a_4 \end{bmatrix} \cdot \begin{bmatrix} I_x \\ I_y \end{bmatrix} \qquad (2)$$

where matrices y and z correspond respectively to the Jones Matrix for the detector 80 of the beam splitter 16 and the focusing lens 50, i.e. the optical elements for the light path after the target. Matrices a and b correspond to the lens system 12, the interference filter 13, polarizer 17 and the beam splitter 16 and the lens 15, that is the optical elements in the light path before the target. Further, the matrix [S] in the center corresponds to the sample W.

In the prior art arrangement of calculating a library for the entire system, the whole chain of matrices in equation (2) is used to calculate the library. However, referring to FIG. 5, in accordance with an embodiment of the invention instead of using the whole chain of matrices shown in equation (2) above to calculate the entries for the library, it is possible to calculate the effect of the Jones Matrices in three stages:

1. the tool dependent Jones matrices before the target;
2. the tool independent Jones matrix of the target itself; and,
3. the tool dependent Jones Matrices after the light has been reflected from the target.

The three stages can be represented by the following:

$$\begin{bmatrix} C_x \\ C_y \end{bmatrix} = \begin{bmatrix} after_1 & after_2 \\ after_3 & after_4 \end{bmatrix} \cdot \begin{bmatrix} S_1 & S_2 \\ S_3 & S_4 \end{bmatrix} \cdot \begin{bmatrix} before_1 & before_2 \\ before_3 & before_4 \end{bmatrix} \cdot \begin{bmatrix} I_x \\ I_y \end{bmatrix} \quad (3)$$

Thus, the tool dependent matrices may be combined into single matrices—one before the light is incident on the target and one after the light has been reflected by the target. To create a tool dependent library, the tool independent matrix is multiplied with the tool dependent matrices. It will be appreciated by one skilled in the relevant art that separate matrices may be required for the light path before and after the target, as the polarization state may change at the target and thus the multiplication is not commutative.

According to an embodiment, by storing the tool-independent library on a central computer, and using the tool-independent library with a specific metrology tool, a tool specific library may be generated quickly for each target for use as the basis of a library search method to determine the target parameters of a measured spectrum. Alternatively, a determined tool specific record may be used as the starting value of an iterative search process. As an additional step, according to an embodiment, interpolation between the records in the tool specific library to combine records which resemble the measurement signal can be performed to get a better estimate of a starting value for the iterative search process.

In an embodiment, a first calculator may be arranged to calculate the first plurality of calibration spectra from the reference pattern, each of the spectra determined using a different known value of a structure parameter of the reference pattern and without taking account parameters of an apparatus used to produce the reference pattern. The first calculator may be configured to determine the tool independent library. A memory may be configured to store a representation of each of the spectra in the first library. Also, a second calculator may be configured to calculate the second plurality of calibration spectra corresponding to at least one of the stored spectra in the first library for a target spectrum using parameters of a measuring apparatus configured to measure the target spectrum. The second calculator may be configured to determine the tool dependent library. A comparator may be configured to compare the measured spectrum and the second plurality of calibration spectra. Further, a processor may be configured to use the comparison to derive a value for the parameter of the target pattern.

In an embodiment, the first and second calculators may be different entities of part of a master calculator. The master calculator may also include the comparator and the processor.

While in the above example, Jones matrices have been used to represent the optical elements, other arrangements such as Mueller matrices are possible. Mueller matrices are 4×4 matrices and are beneficial when dealing with complex optical elements or taking into account subtle errors in the optical elements.

It will be appreciated by one skilled in the relevant art that while the use of separate tool independent and tool specific libraries has particular application with a scatterometer, embodiments of the invention may be used in other applications where it is desired to set up a library of different simulated signals for comparison with a measured set of signals in order to derive a set of parameters.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool, and/or an inspection tool. Where applicable, the disclosure herein may be applied to such and other substrate processing tools. Further, the substrate may be processed more than once, for example, in order to create a multi-layer IC, so that the term substrate used herein may also refer to a substrate that already contains multiple processed layers.

Although specific reference may have been made above to the use of embodiments of the invention in the context of optical lithography, it will be appreciated by one skilled in the relevant art that embodiments of the invention may be used in other applications such as, for example, imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure, or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157, or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

While specific embodiments of the invention have been described above, it will be appreciated that the invention may be practiced otherwise than as described. For example, the invention may take the form of a computer program contain-

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for determining a parameter of a target pattern, the method comprising:
    determining, with a processing device, a first plurality of calibration spectra from a reference pattern, each of the spectra are determined using a different known value of at least one structure parameter of the reference pattern, wherein the first plurality of calibration spectra is independent of parameters of an apparatus used to produce the reference pattern;
    storing a representation of each of the first plurality of calibration spectra in a first library in a memory;
    determining, with the processing device, a second plurality of calibration spectra for a target pattern using at least one of the stored spectra in the first library and parameters of a measuring apparatus configured to measure the target spectrum;
    measuring, with the processing device, a spectrum by directing a beam of radiation onto the target pattern;
    comparing, with the processing device, the measured spectrum and the second plurality of calibration spectra; and
    using, with the processing device, the comparison to derive a value for the parameter of the target pattern.

2. The method according to claim 1, wherein the determining the second plurality of calibration spectra comprises forming a weighted plurality of spectra for the target spectrum corresponding to different combinations of possible radiation parameters used to produce the spectra.

3. The method according to claim 1, wherein the determining the first and second plurality of calibration spectra comprises using Jones matrices for optical elements of the measuring apparatus and the target pattern.

4. The method according to claim 1, wherein the determining the second plurality of calibration spectra comprises using separate Jones matrices formed for optical elements of the measuring apparatus in a path of the beam of radiation before and after the target pattern.

5. The method according to claim 1, further comprising using a scatterometry parameter as the parameter and using a scatterometer as the measuring apparatus.

6. The method according to claim 1, wherein the using the comparison further comprises using the derived value as an initial value to an iterative search method.

7. The method according to claim 1, wherein the determining the second plurality of calibration spectra further comprises storing the second plurality of calibration spectra in a second library.

8. The method according to claim 1, wherein the determining the second plurality of calibration spectra further comprises using separate Mueller matrices for optical elements in a path of the beam of radiation before and after the target pattern.

9. An inspection apparatus configured to determine a value of a parameter of a lithographic process used to manufacture a device layer on a substrate, the apparatus comprising:
    a first calculator configured to determine a first plurality of calibration spectra from a reference pattern, each of the spectra are determined using a different known value of at least one structure parameter of the reference pattern and excluding parameters of an apparatus used to produce the reference pattern;
    a memory configured to store a representation of each of the first plurality of calibration spectra in a first library;
    a second calculator configured to determine a second plurality of calibration spectra corresponding to at least one of the stored spectra in the first library for a target spectrum using parameters of a measuring apparatus configured to measure the target spectrum;
    a measuring device configured to direct a beam of radiation onto the target pattern to produce a spectrum;
    a comparator configured to compare the measured spectrum and the second plurality of calibration spectra; and
    a processor configured to use the comparison from the comparator to derive a value for the parameter of the target pattern.

10. A lithographic apparatus comprising;
    an illumination optical system configured to illuminate a pattern;
    a projection optical system configured to project an image of a pattern onto a substrate; and
    an inspection apparatus configured to determine a value of a parameter of a lithographic process used to manufacture a device layer on the substrate, the apparatus comprising:
    a first calculator configured to calculate a first plurality of calibration spectra from a reference pattern, each of the spectra determined using a different known value of at least one structure parameter of the reference pattern, wherein the first plurality of calibration spectra is independent of parameters of an apparatus used to produce the reference pattern;
    a memory configured to store a representation of each of the first plurality of calibration spectra in a first library;

a second calculator configured to calculate a second plurality of calibration spectra for a target pattern using at least one of the stored spectra in the first library and for a target spectrum using parameters of a measuring apparatus configured to measure the target spectrum;

a measuring device configured to direct a beam of radiation onto the target pattern to produce a spectrum;

a comparator configured to compare the measured spectrum and the second plurality of calibration spectra; and a processor configured to use the comparison from the comparator to derive a value for the parameter of the target pattern.

11. A lithographic cell comprising;

a coater configured to coat a substrate with a radiation sensitive layer;

a lithographic apparatus configured to expose images onto the radiation sensitive layer of the substrate coated by the coater;

a developer configured to develop images exposed by the lithographic apparatus; and an inspection apparatus configured to determine a value of a parameter of a lithographic process used to manufacture a device layer on a substrate, the apparatus comprising:

a first calculator configured to calculate a first plurality of calibration spectra from a reference pattern, each of the spectra determined using a different known value of at least one structure parameter of the reference pattern, wherein the first plurality of calibration spectra is independent of and parameters of an apparatus used to produce the reference pattern;

a memory configured to store a representation of each of the first plurality of calibration spectra in a first library;

a second calculator configured to calculate a second plurality of calibration spectra for a target pattern using at least one of the stored spectra in the first library and parameters of a measuring apparatus used to measure the target spectrum;

a measuring device configured to direct a beam of radiation onto the target pattern to produce a spectrum;

a comparator configured to compare the measured spectrum and the second plurality of calibration spectra; and a processor configured to use the comparison from the comparator to derive a value for the parameter of the target pattern.

12. A computer program embedded in machine readable medium and including machine executable instructions configured to execute a method of determining at least one parameter of a target pattern the method comprising:

determining, with the processing device, a first plurality of calibration spectra from at least one reference pattern, each of the spectra are determined using a different known value of at least one structure parameter of the reference pattern, wherein the first plurality of calibration spectra is independent of and parameters of an apparatus used to produce the reference pattern;

storing a representation of each of the first plurality of calibration spectra in a first library in a memory;

determining, with the processing device, a second plurality of calibration spectra for a target pattern using at least one of the stored spectra in the first library and parameters of a measuring apparatus configured to measure the target spectrum;

combining, with the processing device, the first plurality of calibration spectra and the second plurality of calibration spectra to produce a third plurality of calibration spectra which is representative of a spectra produced by the target spectra using said measuring apparatus;

comparing, with the processing device, a measured target spectrum and the second plurality of calibration spectra; and using, with the processing device, the comparison to derive a value for the parameter of the target pattern.

* * * * *

UNITED STATES PATENT AND TRADEMARK OFFICE
CERTIFICATE OF CORRECTION

PATENT NO. : 7,738,103 B2  Page 1 of 1
APPLICATION NO. : 12/258719
DATED : June 15, 2010
INVENTOR(S) : Kiers et al.

It is certified that error appears in the above-identified patent and that said Letters Patent is hereby corrected as shown below:

In Claim 10, column 15, lines 4-5, please delete "for a target spectrum using".

Signed and Sealed this

Fourteenth Day of September, 2010

David J. Kappos
*Director of the United States Patent and Trademark Office*